US012599344B2

(12) United States Patent
Ninomiya et al.

(10) Patent No.: US 12,599,344 B2
(45) Date of Patent: Apr. 14, 2026

(54) X-RAY CT APPARATUS

(71) Applicant: FUJIFILM Healthcare Corporation, Kashiwa (JP)

(72) Inventors: Hiroaki Ninomiya, Kashiwa (JP); Kana Kobayashi, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 170 days.

(21) Appl. No.: 18/768,235

(22) Filed: Jul. 10, 2024

(65) Prior Publication Data

US 2025/0032059 A1     Jan. 30, 2025

(30) Foreign Application Priority Data

Jul. 26, 2023    (JP) ................................. 2023-121174

(51) Int. Cl.
    A61B 6/03        (2006.01)
    A61B 6/00        (2006.01)
    A61B 6/40        (2024.01)
(52) U.S. Cl.
    CPC .............. A61B 6/032 (2013.01); A61B 6/405 (2013.01); A61B 6/4452 (2013.01)
(58) Field of Classification Search
    None
    See application file for complete search history.

(56) References Cited

U.S. PATENT DOCUMENTS

| | | | |
|---|---|---|---|
| 5,867,555 A | 2/1999 | Popescu et al. | |
| 6,507,639 B1 | 1/2003 | Popescu | |
| 9,867,587 B2 | 1/2018 | O'Donnell | |
| 2004/0131141 A1* | 7/2004 | Horiuchi | A61B 6/542 |
| | | | 378/4 |
| 2008/0232542 A1 | 9/2008 | Lin | |
| 2011/0274240 A1 | 11/2011 | Sugaya et al. | |
| 2017/0000447 A1* | 1/2017 | Profio | A61B 6/461 |
| 2021/0093277 A1* | 4/2021 | Jackson | A61B 6/032 |

FOREIGN PATENT DOCUMENTS

| | | |
|---|---|---|
| DE | 19806063 A1 | 10/1998 |
| WO | WO03/022018 A1 | 3/2003 |
| WO | WO2005099577 A1 | 10/2005 |

OTHER PUBLICATIONS

European search report dated Dec. 6, 2024 in connection with European Patent Application No. 24 18 8149.

* cited by examiner

*Primary Examiner* — Hoon K Song
(74) *Attorney, Agent, or Firm* — Paul Teng

(57)                ABSTRACT

An X-ray CT apparatus includes a rotating plate that causes an X-ray source and an X-ray detector to rotate around a subject, an image generation section that generates a tomographic image of the subject based on a detection signal. A controller controls each unit and has a modulation pattern setting section that sets a modulation pattern used for modulation of an emission dose, which is an X-ray dose emitted from the X-ray source while the rotating plate rotates, such that the emission dose to a site having high radiation sensitivity of the subject is reduced more than the emission dose to other sites, and a modulation pattern adjustment section that adjusts the modulation pattern based on an upper limit speed, which is an upper limit of a modulation speed of the emission dose.

5 Claims, 9 Drawing Sheets

X-RAY CT APPARATUS

CROSS REFERENCE TO RELATED APPLICATION

The present application claims priority from Japanese Patent Application No. 2023-121174, filed on Jul. 26, 2023, the content of which is hereby incorporated by reference into this application.

BACKGROUND OF THE INVENTION

1. Field of the Invention

The present invention relates to an X-ray CT apparatus that captures a tomographic image of a subject, and particularly relates to a technique of reducing exposure of a subject.

2. Description of the Related Art

An X-ray CT apparatus uses projection data from multiple directions that is obtained by rotating, around a subject, an X-ray source that emits an X-ray to the subject and an X-ray detector that detects the X-ray transmitted through the subject to generate a tomographic image of the subject. The generated tomographic image depicts a shape of an organ within the subject and is used for image diagnosis.

Image quality of the tomographic image is improved as a dose of the X-ray emitted to the subject is higher, but an exposure dose to the subject increases. Since the increase in the exposure dose has a bad influence on the subject, it is important to suppress an emission dose, which is an X-ray dose to be emitted, particularly to a site positioned on a body surface and having high radiation sensitivity, such as an eye or a mammary gland.

U.S. Pat. No. 9,867,587A discloses that an emission dose in a case where an X-ray source that rotates around a subject is positioned on a front side of the subject, which is a side of a site having high radiation sensitivity, is reduced as compared with the emission dose in a case where the X-ray source is positioned on a rear side of the subject.

SUMMARY OF THE INVENTION

However, in U.S. Pat. No. 9,867,587A, a method of specifically controlling the emission dose is not sufficiently disclosed, and the emission dose may not be controlled to an instruction value set in advance. That is, since there is an upper limit depending on hardware performance or an upper limit set by an operator in a modulation speed of the emission dose, the emission dose as the instruction value may not be obtained. In a case where the emission dose as the instruction value is not obtained, the reduction in the emission dose to the site having high radiation sensitivity is insufficient, or the image quality of the tomographic image deteriorates due to the shortage of the emission dose.

An object of the present invention is to provide an X-ray CT apparatus capable of maintaining image quality of a tomographic image while reducing an emission dose to a site having high radiation sensitivity.

An X-ray CT apparatus according to an aspect of the present invention comprises an X-ray source that emits an X-ray to a subject, an X-ray detector that detects the X-ray transmitted through the subject, a rotating plate that causes the X-ray source and the X-ray detector to rotate around the subject, an image generation section that generates a tomographic image of the subject based on a detection signal of the X-ray detector, and a controller that controls each unit, in which the controller has a modulation pattern setting section that sets a modulation pattern used for modulation of an emission dose, which is an X-ray dose emitted from the X-ray source while the rotating plate rotates, such that the emission dose to a site having high radiation sensitivity of the subject is reduced more than the emission dose to other sites, and a modulation pattern adjustment section that adjusts the modulation pattern based on an upper limit speed, which is an upper limit of a modulation speed of the emission dose.

According to the present invention, it is possible to provide the X-ray CT apparatus capable of maintaining the image quality of the tomographic image while reducing the emission dose to the site having high radiation sensitivity.

DESCRIPTION OF THE PREFERRED EMBODIMENTS

Hereinafter, examples of an X-ray computed tomography (CT) apparatus according to the embodiments of the present invention will be described with reference to accompanying drawings. The X-ray CT apparatus generates a tomographic image as a medical image used for diagnosis of a subject or the like.

Example 1

Figure 1:
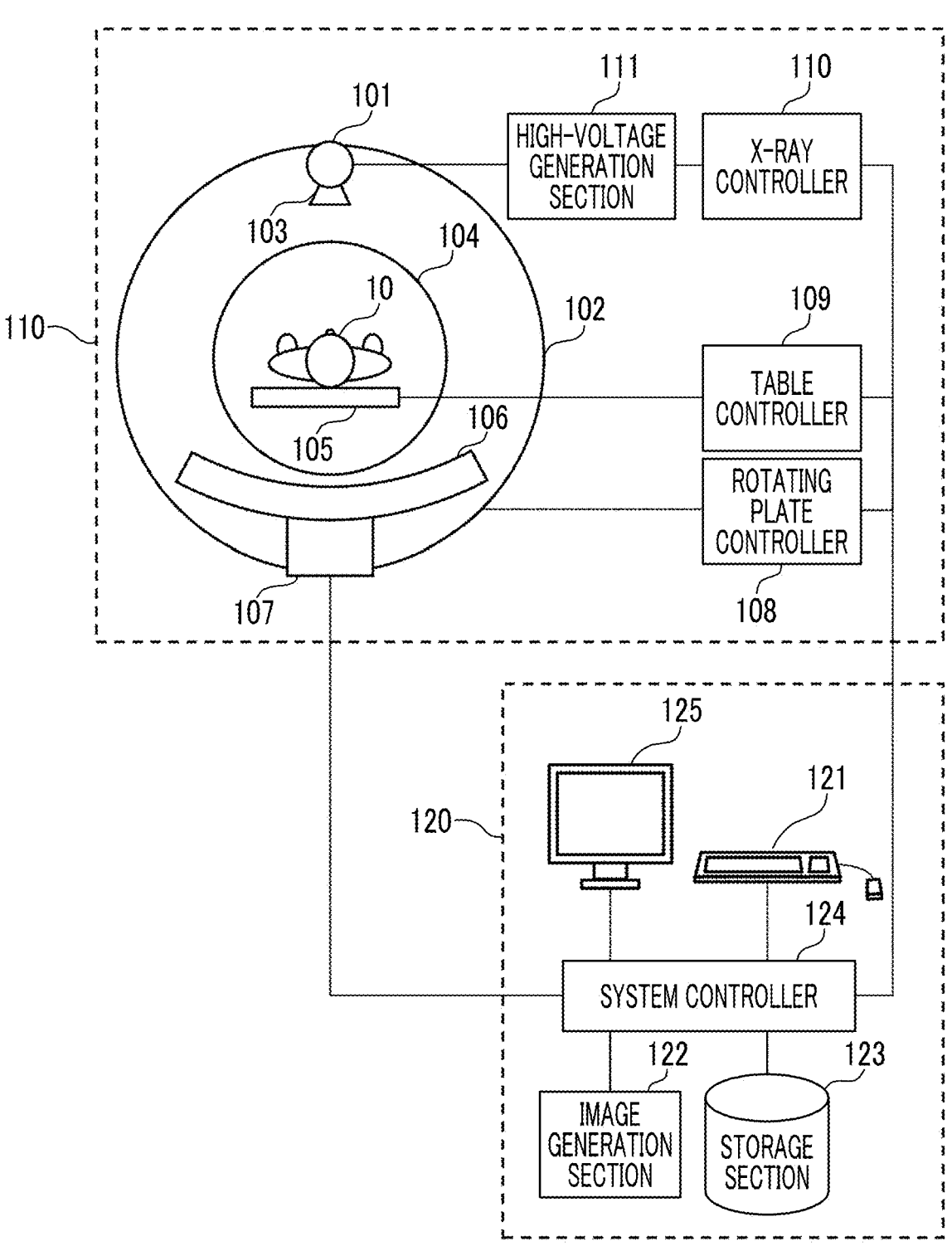
FIG. 1 is a diagram showing an example of an overall configuration of an X-ray CT apparatus of Example 1.

An overall configuration of the X-ray CT apparatus of Example 1 will be described with reference to FIG. 1. The X-ray CT apparatus comprises a scan gantry unit 100 and an operation unit 120. The scan gantry unit 100 is installed in an imaging room surrounded by a shielding material that blocks an X-ray, and the operation unit 120 is installed in an operation room located outside the imaging room.

The scan gantry unit 100 comprises an X-ray source 101, a rotating plate 102, a collimator 103, an X-ray detector 106, a data collection section 107, a table 105, a rotating plate controller 108, a table controller 109, an X-ray controller 110, and a high-voltage generation section 111. The X-ray source 101 is a device that emits the X-ray to a subject 10 placed on the table 105 and is, for example, an X-ray tube device. The collimator 103 is a device that restricts an emission range of the X-ray. The rotating plate 102 is provided with an opening portion 104 through which the subject 10 placed on the table 105 enters, and is also equipped with the X-ray source 101 and the X-ray detector 106 and rotates the X-ray source 101 and the X-ray detector 106 around the subject 10.

The X-ray detector 106 is a device that is disposed to face the X-ray source 101 and comprises a plurality of detection elements that detect the X-ray to acquire a spatial distribution of the X-ray. The detection elements of the X-ray detector 106 are arranged two-dimensionally in a rotation direction and a rotation axis direction of the rotating plate 102. The data collection section 107 is a device that collects the spatial distribution of the X-ray detected by the X-ray detector 106 as digital data.

The rotating plate controller 108 is a device that controls rotation and inclination of the rotating plate 102. The table controller 109 is a device that controls up, down, front, rear, left, and right movements of the table 105. The high-voltage generation section 111 is a power source that generates a tube voltage, which is a voltage applied to the X-ray source 101, and a tube current, which is a current supplied to the X-ray source 101. The X-ray controller 110 is a device that controls an output of the high-voltage generation section 111. The rotating plate controller 108, the table controller 109, and the X-ray controller 110 are, for example, a micro-processing unit (MPU) or the like.

The operation unit 120 comprises an input section 121, an image generation section 122, a display section 125, a storage section 123, and a system controller 124. The input section 121 is a device that is used to input examination data such as a name of the subject 10, an examination date and time, and an imaging condition, and is, for example, a keyboard, a pointing device, a touch panel, or the like. The image generation section 122 is a device that generates the tomographic image by using the digital data collected by the data collection section 107, and is, for example, an MPU, a graphics processing unit (GPU), or the like. The display section 125 is a device that displays the tomographic image or the like generated by the image generation section 122, and is, for example, a liquid crystal display, a touch panel, or the like. The storage section 123 is a device that stores the digital data collected by the data collection section 107, the tomographic image generated by the image generation section 122, a program to be executed by the system controller 124, data to be used by the program, and the like, and is, for example, a hard disk drive (HDD), a solid state drive (SSD), or the like. The system controller 124 is a device that controls each unit such as the rotating plate controller 108, the table controller 109, and the X-ray controller 110, and is, for example, a central processing unit (CPU).

With the generation of the tube voltage and the tube current by the high-voltage generation section 111 based on the imaging condition set via the input section 121, the X-ray according to the imaging condition is emitted from the X-ray source 101 to the subject 10. The X-ray detector 106 detects the X-rays emitted from the X-ray source 101 and transmitted through the subject 10 with a large number of detection elements to acquire the spatial distribution of the transmitted X-rays. The rotating plate 102 is controlled by the rotating plate controller 108 to rotate based on the imaging condition input through the input section 121, particularly a rotation speed or the like. The table 105 is controlled by the table controller 109 and moves relative to the rotating plate 102 to cause an imaging position designated with respect to the subject 10 to move to an imaging field of view, which is a range where the transmitted X-rays are detected.

With repetition of the emission of the X-ray by the X-ray source 101 and the detection of the X-ray by the X-ray detector 106 together with the rotation of the rotating plate 102, projection data, which is an X-ray projection image of the subject 10, is measured at various projection angles. In the projection data, a view representing each projection angle is associated with a channel (ch) number and a column number which are detection element numbers of the X-ray detector 106. The measured projection data is transmitted to the image generation section 122. The image generation section 122 performs back-projection processing on a plurality of pieces of projection data to generate the tomographic image. The generated tomographic image is displayed on the display section 125 or stored in the storage section 123 as the medical image.

In the X-ray CT apparatus, image quality of the generated tomographic image is improved as an emission dose, which is an X-ray dose emitted to the subject 10, is higher, but an exposure dose to the subject 10 increases. Since the increase in the exposure dose has a bad influence on the subject 10, the emission dose is required to be suppressed. In particular, in order to reduce the exposure dose to a site positioned on a body surface and having high radiation sensitivity, such as an eye or a mammary gland, the emission dose to the subject 10 may be modulated during the rotation of the rotating plate 102.

Figure 2:
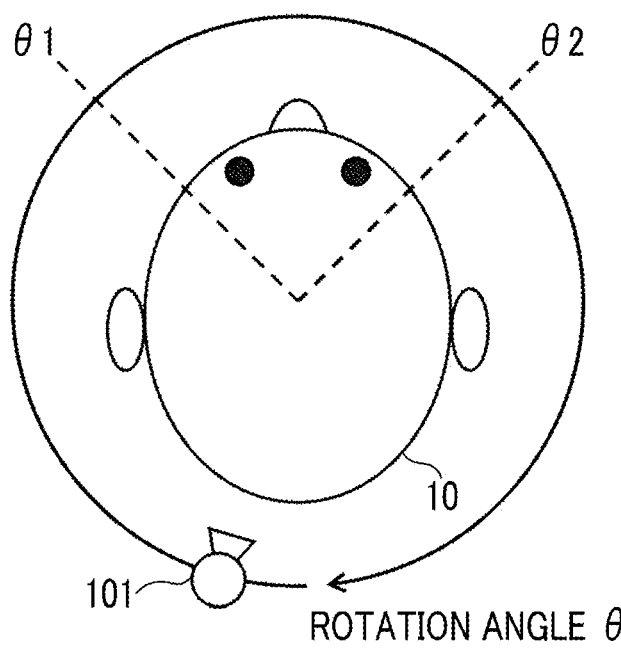
FIG. 2 is a diagram for describing modulation of an emission dose.
Figure 2:
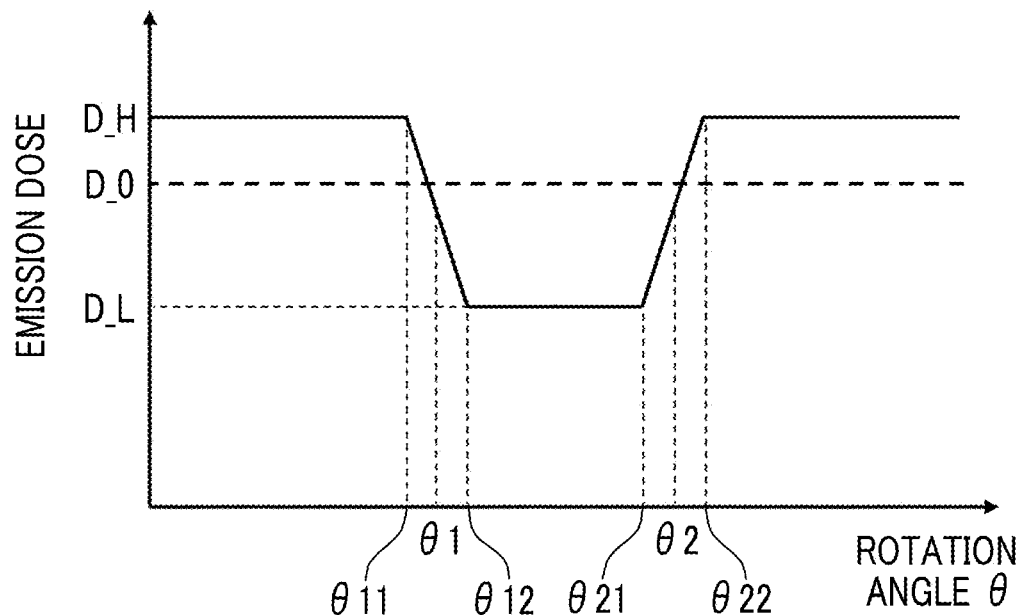

The emission dose modulated during the rotation of the rotating plate 102 will be described with reference to FIG. 2. An upper part of FIG. 2 shows the X-ray source 101 that rotates around a head part of the subject 10. In a case where a rotation angle θ of the X-ray source 101 is in a range from θ1 to θ2, the X-ray is emitted to the eye, which is the site having high radiation sensitivity. Thus, in order to reduce the exposure dose to the eye, the emission dose is modulated in accordance with the rotation angle θ.

A lower part of FIG. 2 shows an example of a modulation pattern of the emission dose by a solid line. The vertical axis is the emission dose, the horizontal axis is the rotation angle θ, and the emission dose before modulation is indicated by a dotted line for comparison. Since the X-ray source 101 rotates at a constant speed, the rotation angle θ is proportional to time. In the modulation pattern exemplified in FIG. 2, the dose amount is set to D_L, which is less than the emission dose D_0 before modulation, at θ12<θ<θ21 such that the exposure dose at θ1<θ<θ2 is reduced. In order to compensate for the reduction in the emission dose in θ12<θ<θ21, the dose amount is set to D_H, which is larger than the emission dose D_0 before modulation in θ<θ11 and θ22<θ. Further, the emission dose changes from D_H to D_L in θ11<θ<θ12, and the emission dose changes from D_L to D_H in θ21<θ<θ22.

Meanwhile, since there is the upper limit depending on the hardware performance in the modulation speed of the emission dose, due to delay in the change in the emission dose from D_H to D_L or from D_L to D_H, the reduction in the exposure dose may be insufficient, or the image quality of the tomographic image may deteriorate. In Example 1, the modulation pattern is adjusted in which the emission dose to the site having high radiation sensitivity is set to be lower than the emission dose to other sites, based on an upper limit speed that is the upper limit of the modulation speed of the emission dose. With the adjustment of the modulation pattern based on the upper limit speed, it is possible to maintain the image quality of the tomographic image while reducing the emission dose to the site having high radiation sensitivity.

Figure 3:
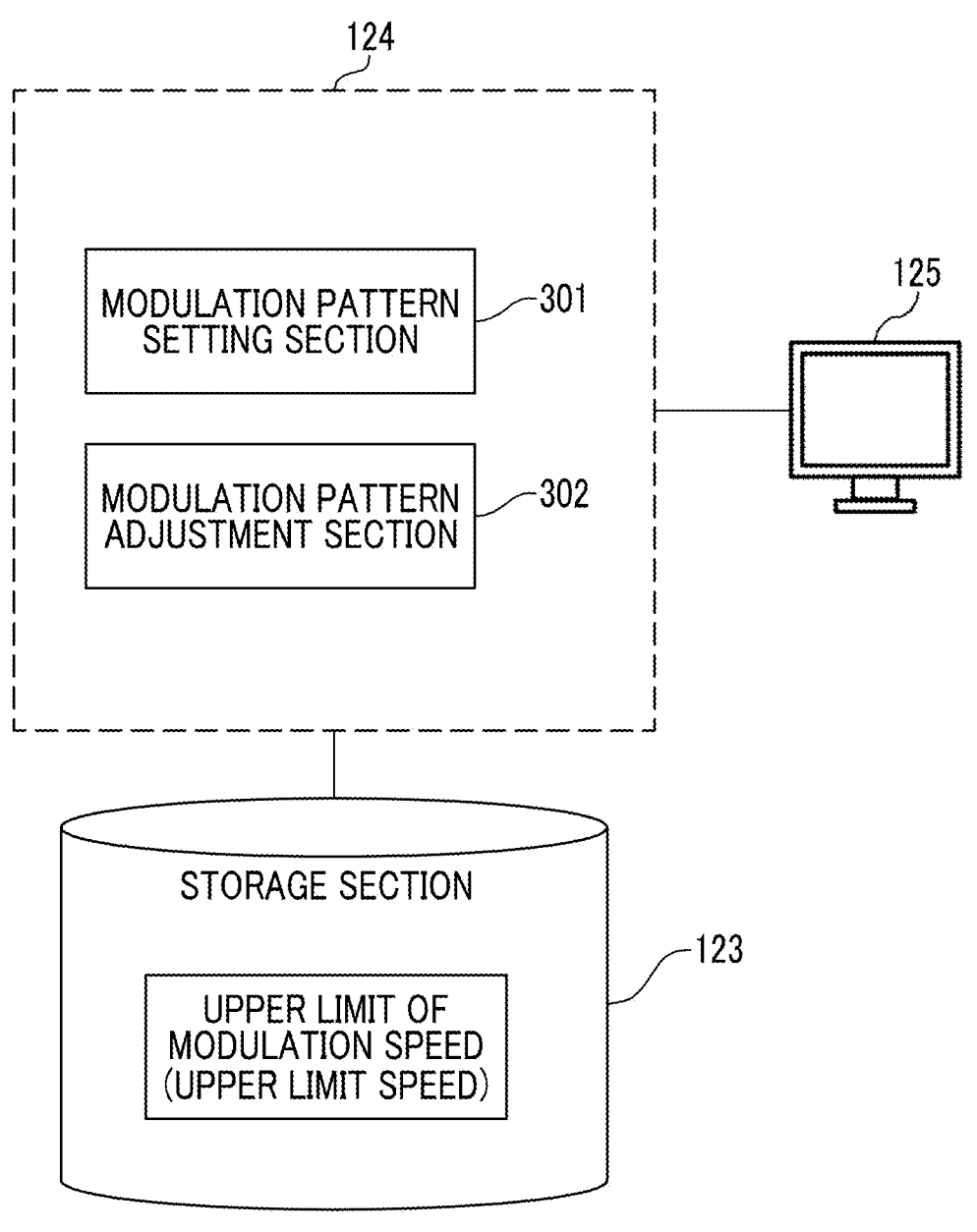
FIG. 3 is a diagram showing an example of functional blocks of Example 1.

Functional blocks of Example 1 will be described with reference to FIG. 3. It should be noted that these functional blocks may be configured with dedicated hardware using an application specific integrated circuit (ASIC), a field-programmable gate array (FPGA), or the like, or may be configured with software that operates on the system controller 124. In the following description, a case where the functional blocks of Example 1 are configured with software will be described.

In Example 1, a modulation pattern setting section 301 and a modulation pattern adjustment section 302 are provided. Hereinafter, each unit will be described. The storage section 123 stores in advance the upper limit speed, which is the upper limit of the modulation speed of the emission dose.

The modulation pattern setting section 301 sets the modulation pattern used for the modulation of the emission dose, which is the X-ray dose emitted to the subject 10 from the X-ray source 101 while the rotating plate 102 rotates. In the modulation pattern set by the modulation pattern setting section 301, as exemplified in FIG. 2, the emission dose to the site having high radiation sensitivity, for example, an eye or a mammary gland is reduced as compared with the emission dose to other sites. Further, the modulation pattern may be set such that a transmitted X-ray dose at each rotation angle is leveled. With the leveling of the transmitted X-ray dose, balance between the image quality of the tomographic image and the exposure dose to the subject is maintained. The modulation pattern set by the modulation pattern setting section 301 may be displayed on the display section 125.

The modulation pattern adjustment section 302 reads out the upper limit speed, which is the upper limit of the modulation speed of the emission dose, from the storage section 123, and adjusts the modulation pattern set by the modulation pattern setting section 301 based on the upper limit speed. The upper limit speed is calculated based on a result of measuring a temporal change of the emission dose in advance, and is stored in the storage section 123.

Figure 4:
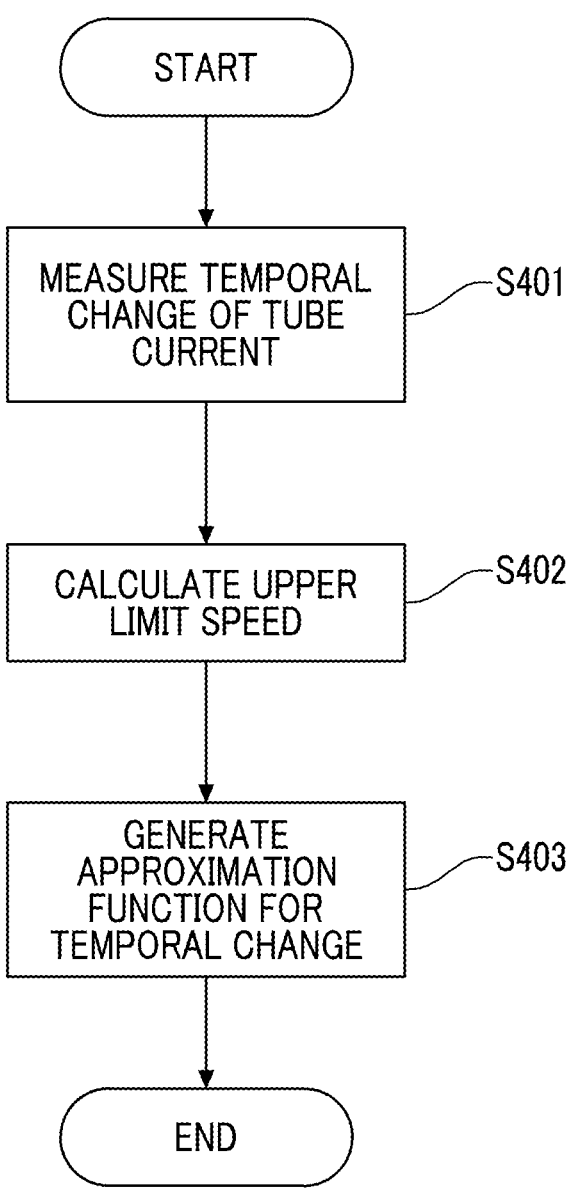
FIG. 4 is a diagram showing an example of a flow of processing of calculating an upper limit speed of the emission dose.

An example of a flow of processing of calculating the upper limit speed of the emission dose will be described step by step with reference to FIG. 4.

S401

The system controller 124 measures the temporal change of the tube current, which is the current supplied to the X-ray source 101. Since the emission dose is proportional to the tube current, the temporal change of the tube current corresponds to the temporal change of the emission dose. Since the modulation speed is different between a case where the tube current increases and a case where the tube current decreases, the temporal change is measured in each of the case where the tube current increases and the case where the tube current decreases.

Figure 5:
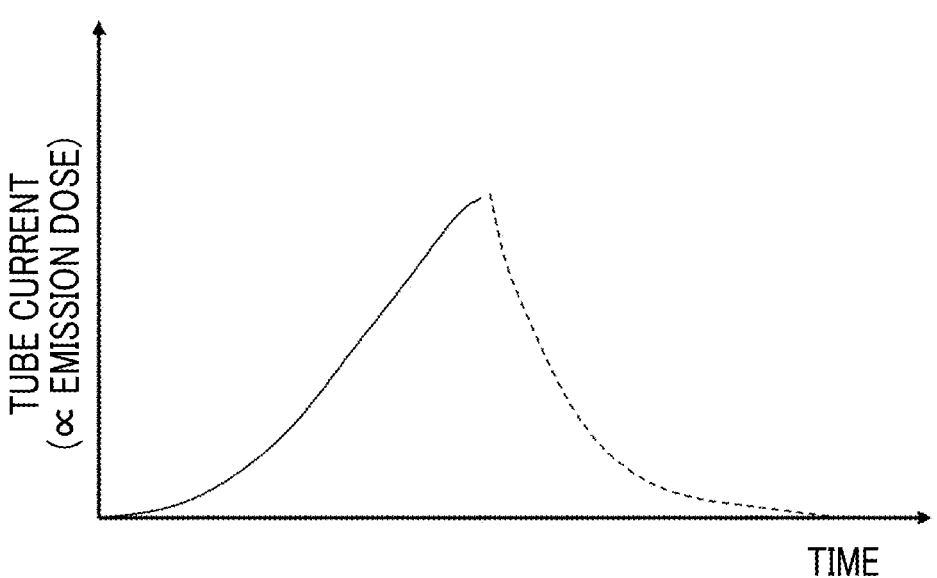
FIG. 5 is a graph showing an example of a result of measuring a temporal change of a tube current.

FIG. 5 is an example of the result of measuring the temporal change of the tube current, in which a solid line indicates the case where the tube current increases and a dotted line indicates the case where the tube current decreases. The temporal change at the time of the increase is measured by setting an instruction value of the tube current to a maximum value in a case where the tube current is zero. The temporal change at the time of the decrease is measured by setting the instruction value of the tube current to zero in a case where the tube current has a maximum value.

S402

The system controller 124 calculates the upper limit speed by using the temporal change measured in S401. Since an inclination at each point of the temporal change exemplified in FIG. 5 indicates the upper limit of the modulation speed of the tube current, the upper limit speeds are calculated for respective tube current values at the time of the increase and at the time of the decrease. The upper limit speeds at the time of the increase and at the time of the decrease, which are calculated for respective tube current values, are stored in the storage section 123.

S403

The system controller 124 generates an approximation function for the temporal change measured in S401. For example, a quadratic function such as the following equation is used as the approximation function.

$$K\_up = A\_up \cdot t^\wedge 2 + B\_up \cdot t + C\_up \qquad \text{(Equation 1)}$$

Here, tis a time, K_up(t) is the temporal change of the tube current at the time of the increase, and A_up, B_up, and C_up are coefficients.

With the generation of the approximation function exemplified by Equation 1, it is sufficient that the coefficient is stored instead of the upper limit speed for each tube current value. Therefore, it is possible to reduce a capacity of the storage section 123. In order to improve the accuracy of the approximation function, a logarithm or a square root of the tube current may be combined.

The upper limit speed, which is the upper limit of the modulation speed of the emission dose, is calculated by the flow of the processing described with reference to FIG. 4 and is stored in the storage section 123. The upper limit speed stored in the storage section 123 is used for adjusting the modulation pattern used for the modulation of the emission dose during the rotation of the rotating plate 102.

An example of a flow of processing of Example 1 will be described step by step with reference to FIG. 6.

S601

The modulation pattern setting section 301 sets the modulation pattern of the emission dose such that the emission dose to the site having high radiation sensitivity is reduced as compared with the emission dose to other sites.

Figure 7:
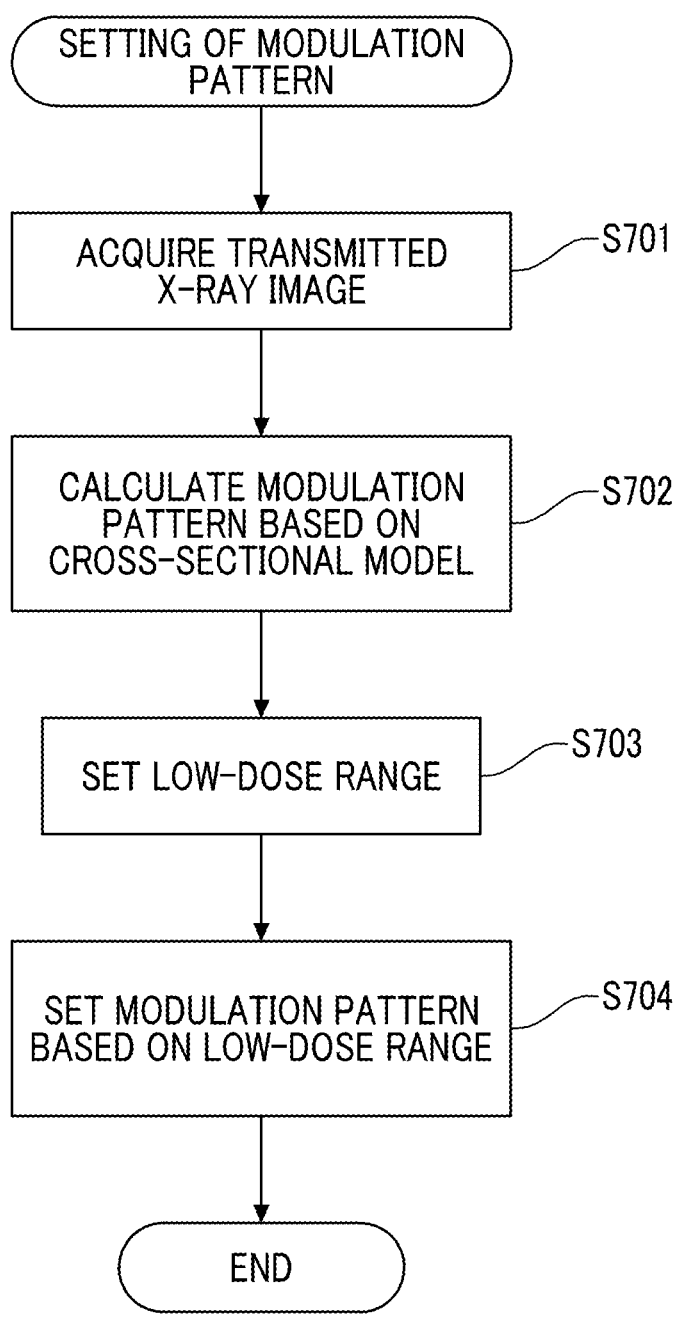
FIG. 7 is a diagram showing an example of a flow of processing of setting a modulation pattern of the emission dose.

An example of the flow of the processing of S601 will be described step by step with reference to FIG. 7.

S701

The system controller 124 acquires a transmitted X-ray image of the subject 10. The transmitted X-ray image acquired in S701 is referred to as a scanogram image or a scout image, and is used to set a range to be CT-imaged.

S702

The system controller 124 creates a cross-sectional model of the subject 10 using the transmitted X-ray image acquired in S701, and calculates the modulation pattern of the emission dose based on the cross-sectional model. The cross-sectional model is a model in which a cross-sectional shape of the subject 10 is approximated to, for example, an ellipse. With the creation of the cross-sectional model, it is possible to calculate an X-ray transmission length through a rotation center of the rotating plate 102 for each rotation angle. The modulation pattern of the emission dose is calculated such that the transmitted X-ray dose with respect to the X-ray transmission length calculated for each rotation angle is leveled. In a case where the cross-sectional shape of the subject 10 can be regarded as a perfect circle, the modulation pattern of the emission dose is constant regardless of the rotation angle θ as indicated by a dotted line in the lower part of FIG. 2. The processing of S702 is not always required.

S703

The modulation pattern setting section 301 acquires a low-dose range that is a range where the emission dose is reduced. The low-dose range may be set, to the transmitted X-ray image acquired in S701, by the operator using the input section 121 or by the system controller 124 using an image recognition function. The set low-dose range is acquired by the modulation pattern setting section 301.

S704

The modulation pattern setting section 301 sets the modulation pattern of the emission dose based on the low-dose range acquired in S703. The modulation pattern set by the modulation pattern setting section 301 is, for example, as shown by a solid line in the lower part of FIG. 2. The modulation pattern is preferably set such that a total amount of the emission dose during one rotation of the rotating plate 102 is the same before and after the modulation. In a case where the total amount of the emission dose is difficult to be maintained before and after the modulation, the modulation pattern may be set such that a difference in the total amount of the emission dose before and after the modulation is less than a predetermined threshold value. Further, the reduction in the emission dose in $\theta 11 < \theta < \theta 22$ may be compensated for an increase in the emission dose in $\theta 11 + \pi < \theta < \theta 22 + \pi$. Return to the description of FIG. 6.

S602

The modulation pattern adjustment section 302 adjusts the modulation pattern set in S601 based on the upper limit speed, which is the upper limit of the modulation speed of the emission dose.

Figure 8:
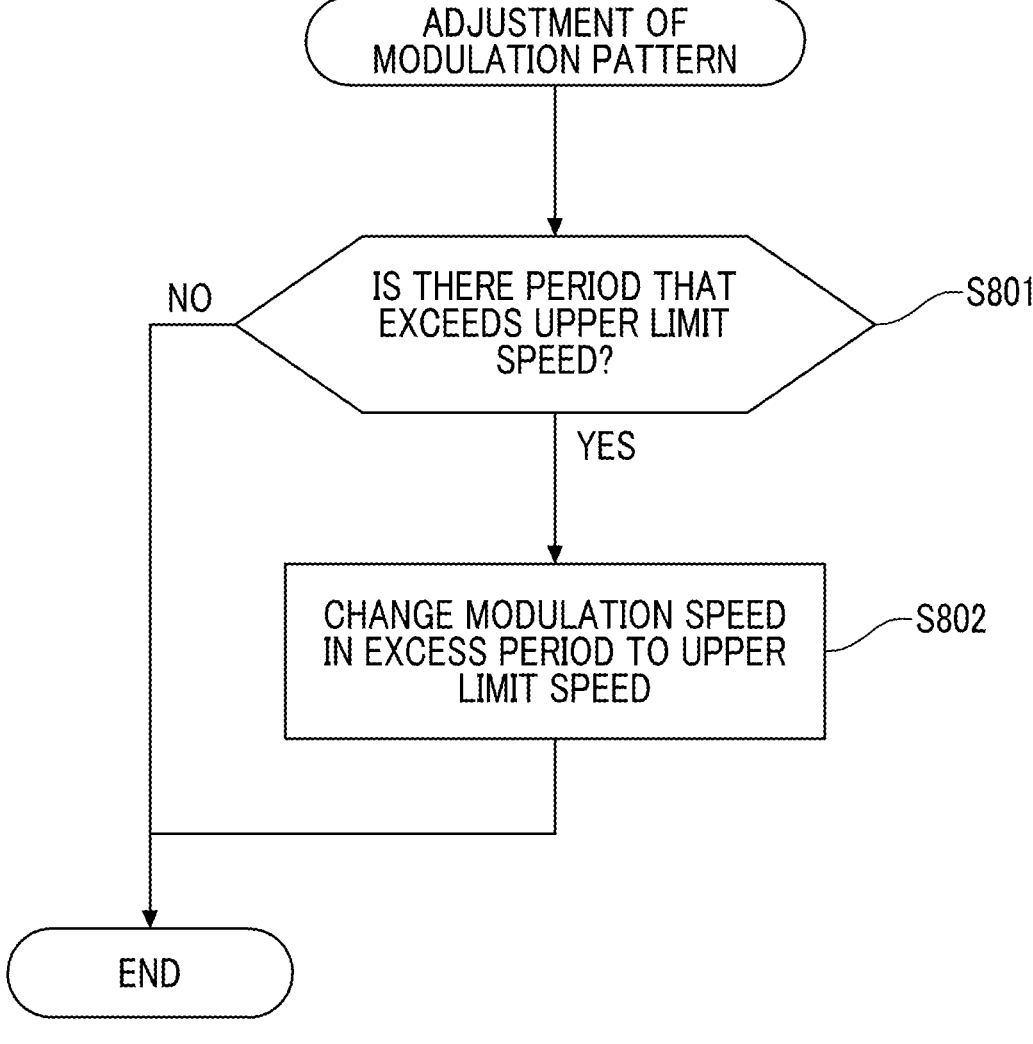
FIG. 8 is a diagram showing an example of a flow of processing of adjusting a set modulation pattern.

An example of the flow of the processing of S602 will be described step by step with reference to FIG. 8.

S801

The modulation pattern adjustment section 302 determines whether or not there is a period of the modulation speed that exceeds the upper limit speed in the modulation pattern set in S601. The determination of whether or not there is an excess period which is the period in which the modulation speed exceeds the upper limit speed is performed at a time of a decrease in the emission dose and at a time of an increase in the emission dose. In a case where there is the excess period in the modulation pattern, the processing proceeds to S802. In a case where there is no excess period, the flow of the processing ends.

S802

The modulation pattern adjustment section 302 changes, to the upper limit speed, the modulation speed in the excess period determined to be the period in which the upper limit speed is exceeded in S801. With the change of the modulation speed in the excess period to the upper limit speed, it is possible to prevent the reduction of the emission dose to the site having high radiation sensitivity from being insufficient.

In a case where the modulation speed in the excess period is changed to the upper limit speed, the total amount of the emission dose during one rotation of the rotating plate 102 is reduced. Therefore, the emission dose to the site other than the site having high radiation sensitivity may be increased to maintain the total amount of the emission dose. With the maintained total amount of the emission dose during one rotation of the rotating plate 102, it is possible to suppress the deterioration in image quality of the tomographic image.

Figure 9:
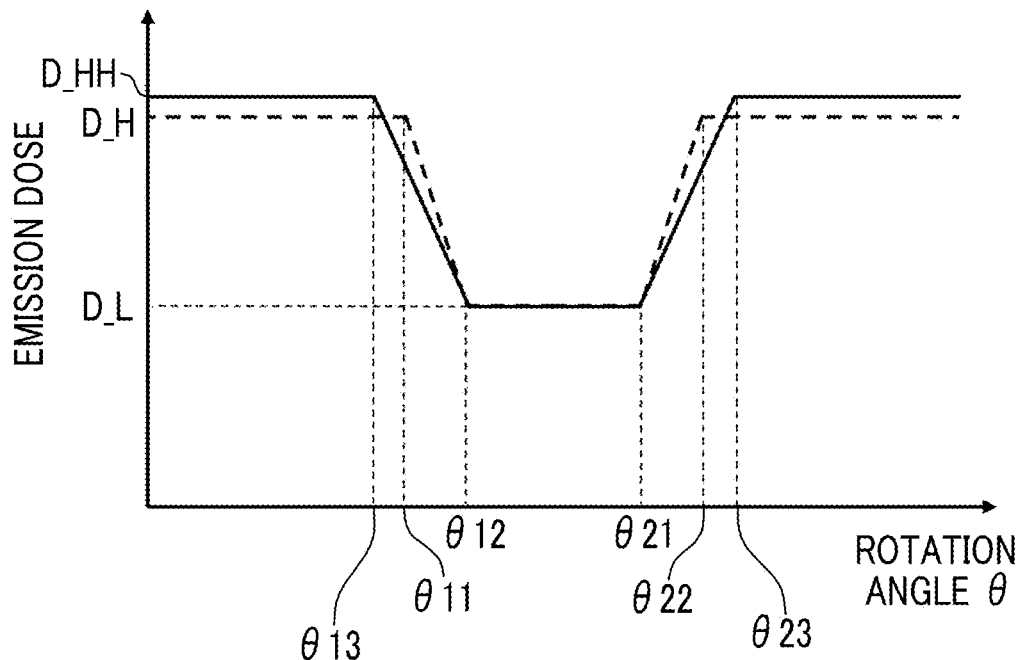
FIG. 9 is a graph for describing the adjustment of the modulation pattern.

The adjustment of the modulation pattern will be described with reference to FIG. 9. In FIG. 9, the modulation pattern before the adjustment is indicated by a dotted line, and the modulation pattern after the adjustment is indicated by a solid line. The modulation pattern before the adjustment is the same as the solid line in the lower part of FIG. 2. Further, the modulation speed corresponds to the inclination of the emission dose with respect to the rotation angle.

In the modulation pattern before the adjustment, the modulation speed in the period of $\theta 11 < \theta < \theta 12$ exceeds the upper limit speed at the time of the decrease and the modulation speed in the period of $\theta 21 < \theta < \theta 22$ exceeds the upper limit speed at the time of the increase. Thus, the modulation speed in each of the excess periods is changed to the upper limit speed. The period of $\theta 12 < \theta < \theta 21$ is not changed such that the emission dose to the site having high radiation sensitivity is maintained as D_L, and the period in which the emission dose changes is $\theta 13 < \theta < \theta 12$ and $\theta 21 < \theta < \theta 23$. Further, in order to compensate for the decrease in the emission dose due to the change in the modulation speed in the excess period, the emission dose in $\theta < \theta 13$ and $\theta 23 < \theta$ is increased from D_H to D_HH.

In a case where the emission dose D_HH to the site other than the site having high radiation sensitivity exceeds a maximum output of the high-voltage generation section 111 or a threshold value set by the operator, the emission dose D_L to the site having high radiation sensitivity may be increased. With the increase in the emission dose D_L to the site having high radiation sensitivity, even in a case where the emission dose to the site other than the site having high radiation sensitivity is insufficient, it is possible to maintain the image quality of the tomographic image. Further, in a case where the emission dose D_L to the site having high radiation sensitivity is less than a minimum output of the high-voltage generation section 111 or a threshold value set by the operator, the emission dose to the site other than the site having high radiation sensitivity may be reduced. With the reduced emission dose to the site other than the site having high radiation sensitivity, it is possible to reduce the exposure dose to the subject 10.

Figure 6:
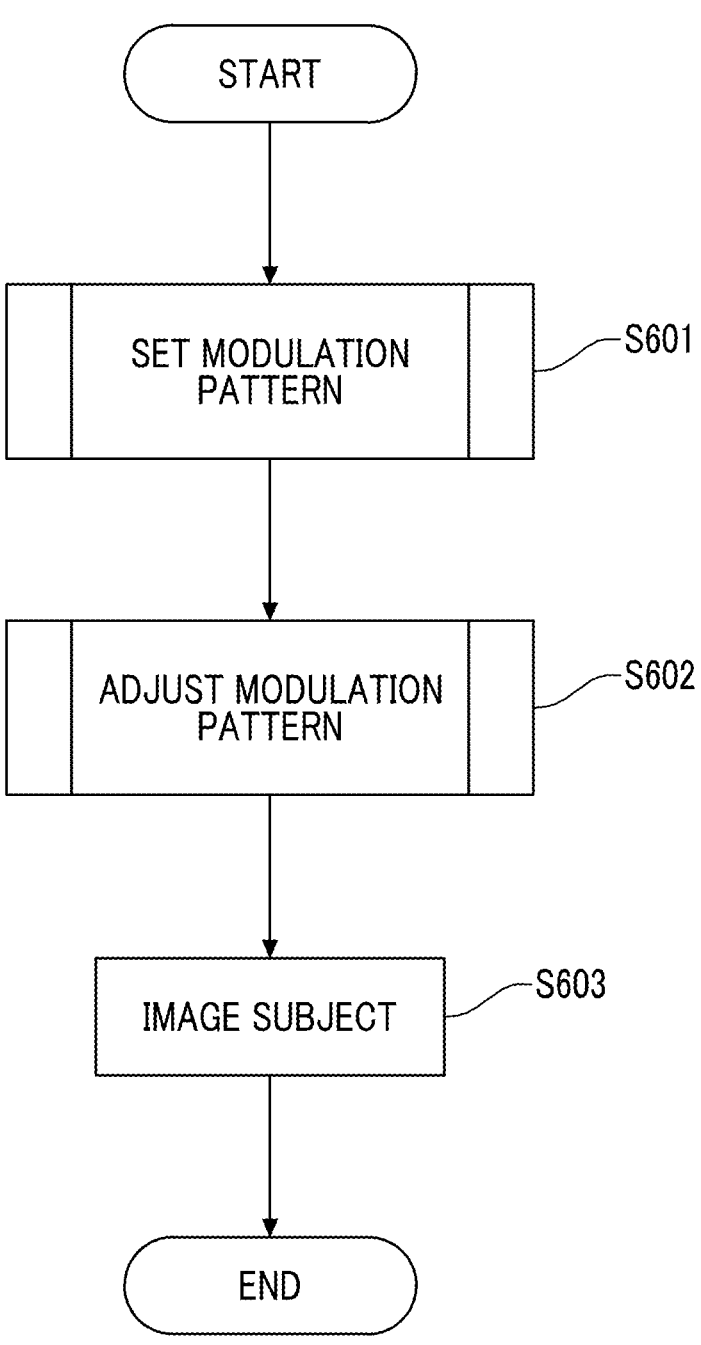
FIG. 6 is a diagram showing an example of a flow of processing of Example 1.

Return to the description of FIG. 6.

S603

The system controller 124 images the subject 10 using the modulation pattern adjusted in S602.

The subject 10 is imaged using the modulation pattern adjusted in accordance with the upper limit speed of the modulation speed of the emission dose by the flow of the processing described with reference to FIG. 6. Therefore, it is possible to maintain the image quality of the tomographic image while reducing the emission dose to the site having high radiation sensitivity.

The embodiments of the present invention have been described above. The present invention is not limited to the above-described embodiments, and the components can be modified and embodied without departing from the gist of the invention. Additionally, a plurality of components disclosed in the above-described embodiments may be combined as appropriate. Furthermore, some components may be deleted from all the components described in the above-described embodiments.

EXPLANATION OF REFERENCES

10: subject
100: scan gantry unit
101: X-ray source
102: rotating plate
103: collimator
104: opening portion
105: table
106: X-ray detector

107: data collection section
108: rotating plate controller
109: table controller
110: X-ray controller
111: high-voltage generation section
120: operation unit
121: input section
122: image generation section
123: storage section
124: system controller
125: display section
301: modulation pattern setting section
302: modulation pattern adjustment section

What is claimed is:

1. An X-ray CT apparatus comprising:

an X-ray source that emits an X-ray to a subject;

an X-ray detector that detects the X-ray transmitted through the subject;

a rotating plate that causes the X-ray source and the X-ray detector to rotate around the subject;

an image generation section that generates a tomographic image of the subject based on a detection signal of the X-ray detector; and a controller that controls each unit, wherein the controller has a modulation pattern setting section that sets a modulation pattern used for modulation of an emission dose, which is an X-ray dose emitted from the X-ray source while the rotating plate rotates, such that the emission dose to a site having high radiation sensitivity of the subject is reduced more than the emission dose to other sites, and a modulation pattern adjustment section that adjusts the modulation pattern based on an upper limit speed, which is an upper limit of a modulation speed of the emission dose.

2. The X-ray CT apparatus according to claim 1, wherein the modulation pattern adjustment section changes the modulation speed exceeding the upper limit speed to the upper limit speed in the modulation pattern set by the modulation pattern setting section.

3. The X-ray CT apparatus according to claim 2, wherein the modulation pattern adjustment section increases the emission dose to the other sites such that a total amount of the emission dose, which is decreased by the change of the modulation speed, is compensated.

4. The X-ray CT apparatus according to claim 3, wherein the modulation pattern adjustment section increases the emission dose to the site having high radiation sensitivity in a case where the emission dose to the other sites exceeds an upper limit value.

5. The X-ray CT apparatus according to claim 3, wherein the modulation pattern adjustment section decreases the emission dose to the other sites in a case where the emission dose to the site having high radiation sensitivity is less than a lower limit value.

* * * * *